United States Patent
Perng et al.

(10) Patent No.: US 7,618,585 B2
(45) Date of Patent: Nov. 17, 2009

(54) FUEL-CONCENTRATION DETECTING AND CONTROLLING DEVICE FOR FUEL CELL

(75) Inventors: Kang-Nang Perng, Sanyi Township, Miaoli County (TW); Ching-Shih Liu, Longtan Township, Taoyuan County (TW); Kin-Fu Lin, Taipei (TW); Charn-Ying Chen, Taoyuan (TW); Kang-Lin Hwang, Sanyi Township, Miaoli County (TW); Ying-Sheng Lee, Sindian (TW)

(73) Assignee: Atomic Energy Council - Institute of Nuclear Energy Research, Taoyuan (TW)

( * ) Notice: Subject to any disclaimer, the term of this patent is extended or adjusted under 35 U.S.C. 154(b) by 821 days.

(21) Appl. No.: 11/205,098

(22) Filed: Aug. 17, 2005

(65) Prior Publication Data

US 2007/0041872 A1     Feb. 22, 2007

(51) Int. Cl.
  *G01N 29/30*  (2006.01)
  *G01N 33/22*  (2006.01)
  *G01N 29/024* (2006.01)

(52) U.S. Cl. .................. 422/62; 73/61.45; 73/61.49; 73/61.61; 73/61.79; 73/571; 73/597; 422/68.1; 429/12; 436/55; 436/131

(58) Field of Classification Search ............ 73/61.45, 73/61.49, 61.61, 61.79, 571, 597; 422/62, 422/68.1; 429/12–14; 436/55, 131
See application file for complete search history.

(56) References Cited

U.S. PATENT DOCUMENTS

| | | | | |
|---|---|---|---|---|
| 3,973,430 A | * | 8/1976 | Cirulis et al. | ............... 73/61.49 |
| 4,934,177 A | * | 6/1990 | Cuthbertson et al. | ........ 73/32 A |
| 5,473,934 A | * | 12/1995 | Cobb | ......................... 73/61.49 |
| 6,194,215 B1 | * | 2/2001 | Rauh et al. | ................... 436/55 |
| 6,295,873 B1 | * | 10/2001 | Condreva | ..................... 73/597 |
| 6,748,793 B2 | * | 6/2004 | Rabinovich et al. | ........ 73/61.45 |
| 7,205,060 B2 | * | 4/2007 | Kaye et al. | ..................... 429/25 |
| 7,263,882 B2 | * | 9/2007 | Sparks et al. | ............ 73/204.26 |
| 7,353,696 B2 | * | 4/2008 | Luo et al. | .................. 73/61.61 |
| 2003/0121315 A1 | * | 7/2003 | Rabinovich et al. | ........ 73/61.45 |
| 2006/0216557 A1 | * | 9/2006 | Miyamoto et al. | ............ 429/22 |

FOREIGN PATENT DOCUMENTS

| | | | |
|---|---|---|---|
| DE | 3009566 | * | 9/1981 |
| DE | 10035624 | * | 2/2002 |

(Continued)

OTHER PUBLICATIONS

Carstensen, E. L., Journal of the Acoustical Society of America 1954, 26, 858-861.*

(Continued)

*Primary Examiner*—Arlen Soderquist

(57) ABSTRACT

An ultrasonic wave passes different fuels of different concentrations with different velocities. The present invention provides a detecting and controlling device where, by a non-touching method, a velocity for an ultrasonic wave in a first fuel with a first fuel concentration is measured. The velocity obtained is taken for a comparison with another velocity for the same ultrasonic wave in a fuel with a default fuel concentration so that the first fuel concentration of the fuel can be under controlled.

5 Claims, 2 Drawing Sheets

FOREIGN PATENT DOCUMENTS

Figure 1:
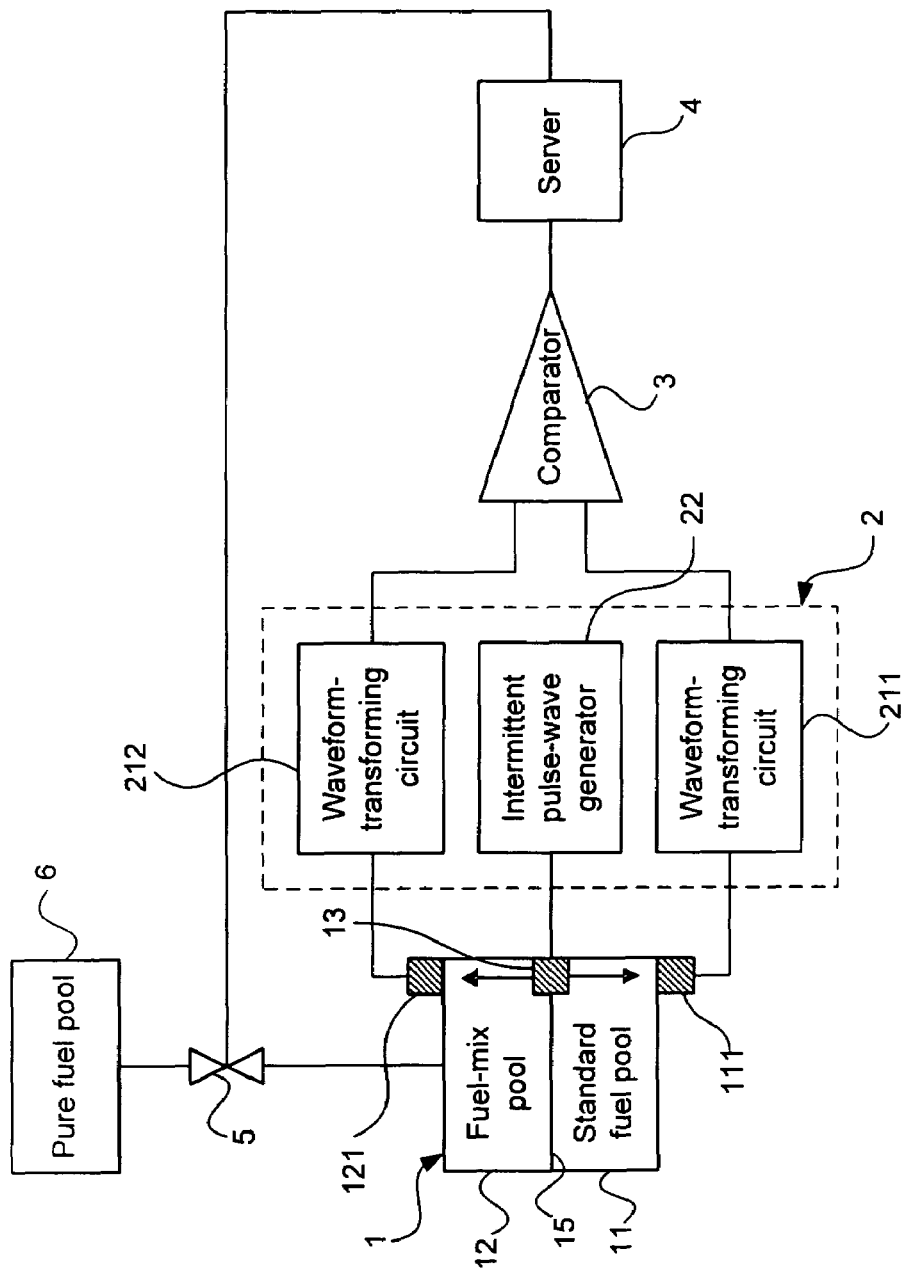

EP     1205748    *   5/2002
EP     1722433    *   11/2006

OTHER PUBLICATIONS

Carstensen, E. L., Journal of the Acoustical Society of America 1954, 26, 862-864.*

Sukackas, V. et al, Nauchnye Trudy Vysshikh Uchebnykh Zavedenii Litovskoi SSR, Ul'trazvuk 1972, 4, 25-32.*

Mitaku, S. et al, Review of Scientific Instruments 1977, 48, 647-650.*

Elias, J. G. et al, Review of Scientific Instruments 1979, 50, 1299-1302.*

Toda, K., Journal of Applied Physics 1981, 52, 652-654.*

Lautscham, K. et al, Measurement Science and Technology 2000, 11, 1432-1439.*

Ikeda, K., Proceedings of the IEEE International Frequency Control Symposium & PDA Exhibition, Seattle, WA, United States, Jun. 6-8, 2001, 474-481, Publishers: Institute of Electrical and Electronics Engineers, New York, N. Y.*

Siegert, H., Acustica 1963, 13, 48-57.*

Stripinis, R. et al, Nauchnye Trudy Vysshikh Uchebnykh Zavedenii Litovskoi SSR, Ul'trazvuk 1969, 117-125.*

* cited by examiner

FUEL-CONCENTRATION DETECTING AND CONTROLLING DEVICE FOR FUEL CELL

FIELD OF THE INVENTION

The present invention relates to a detecting and controlling device; more particularly, relates to emitting an intermittent pulse wave by a transducer element to pass through a fuel pool and be reflected back to be received by a comparator for a time-deviation comparison with a base signal representing a standard fuel concentration or a default acoustic velocity, where the time deviation obtained can be turned into a control signal to remain a fuel concentration of the fuel pool with a valve or a pump.

DESCRIPTION OF THE RELATED ARTS

Following the development of the modern science, the consumption of the natural resources are increasing. To solve the energy problem, a fuel cell with high effectiveness and low pollutant is disclosed as a substitute to the internal combustion engine. In 1957, Willard T. Grubb proclaimed a Proton Exchange Membrane Fuel Cell (PEMFC). But, the PEMFC uses hydrogen as a fuel which is either stored in a gas cylinder with high pressure and so is of high danger; or, it may use the Hydrogen Storage Alloy to provide hydrogen which is too heavy and is inconvenient for supplying.

To solve the above problem, a Direct Methanol Fuel Cell (DMFC) using a methanol solution as a fuel is provided with easy supplying and high safety. Although the DMFC comprises a small volume and a steady and long-term power supply, its power-generating efficiency is much lower than that of the PEMFC, which reaches only one-fifth to one-third of that of the PEMFC. In addition, the methanol crossover of the methanol solution directly affects the DMFC's efficiency. The concentration and the temperature of the methanol solution also directly affect the output efficiency of the electrical energy. It means that, under different temperatures or different concentrations of the methanol solution, deviations of the output current density will happen. Furthermore, the method for sensing the concentration of the methanol solution in the DMFC is based on electrochemistry. After a certain period of time, carbon monoxide will be produced to poison the platinum electrode so that the sensor has to be replaced regularly resulting in cost increase. Moreover, the sensor for electrochemistry comprises a big volume, which is not suitable to the minimization of the DMFC power system's volume. So, the prior arts do not fulfill users' requests on actual use.

SUMMARY OF THE INVENTION

Therefore, the main purpose of the present invention is to provide a detecting and controlling device of low cost for the fuel concentration of a fuel cell.

To achieve the above purpose, the present invention is a fuel-concentration detecting and controlling device for a fuel cell, comprising a comparative fuel pool, a comparator, a server, a controlling device and a pure fuel pool, where the comparative fuel pool comprises a standard fuel pool and a fuel-mix pool; the controlling device is a controlling valve and/or pump; the standard fuel pool and the fuel-mix pool are each connected to a waveform transforming circuit respectively; a first and a second transducer elements are respectively deposed between places where the standard fuel pool and the fuel-mix pool are connected with the waveform-transforming circuits; a time deviation is obtained by a comparator through a comparison of different arriving times of an ultrasonic wave passing through the standard fuel pool and the fuel-mix pool with different fuel concentrations; a control signal based on the time deviation is sent to drive the controlling device by the server to add a fuel (such as a methanol solution) from the pure fuel pool into the fuel-mix pool for balancing the fuel concentrations of the standard fuel pool and the fuel-mix pool between 3.5% and 4%; the first and the second transducer elements are sensors of ultrasonic element provided with tiny electricity for reducing cost and minimizing the concentration variation of the fuel-mix pool; and, the ultrasonic element is made through a micro-machine production for a volume minimization. Accordingly, a novel fuel-concentration detecting and controlling device for a fuel cell is obtained.

BRIEF DESCRIPTIONS OF THE DRAWINGS

Figure 2:
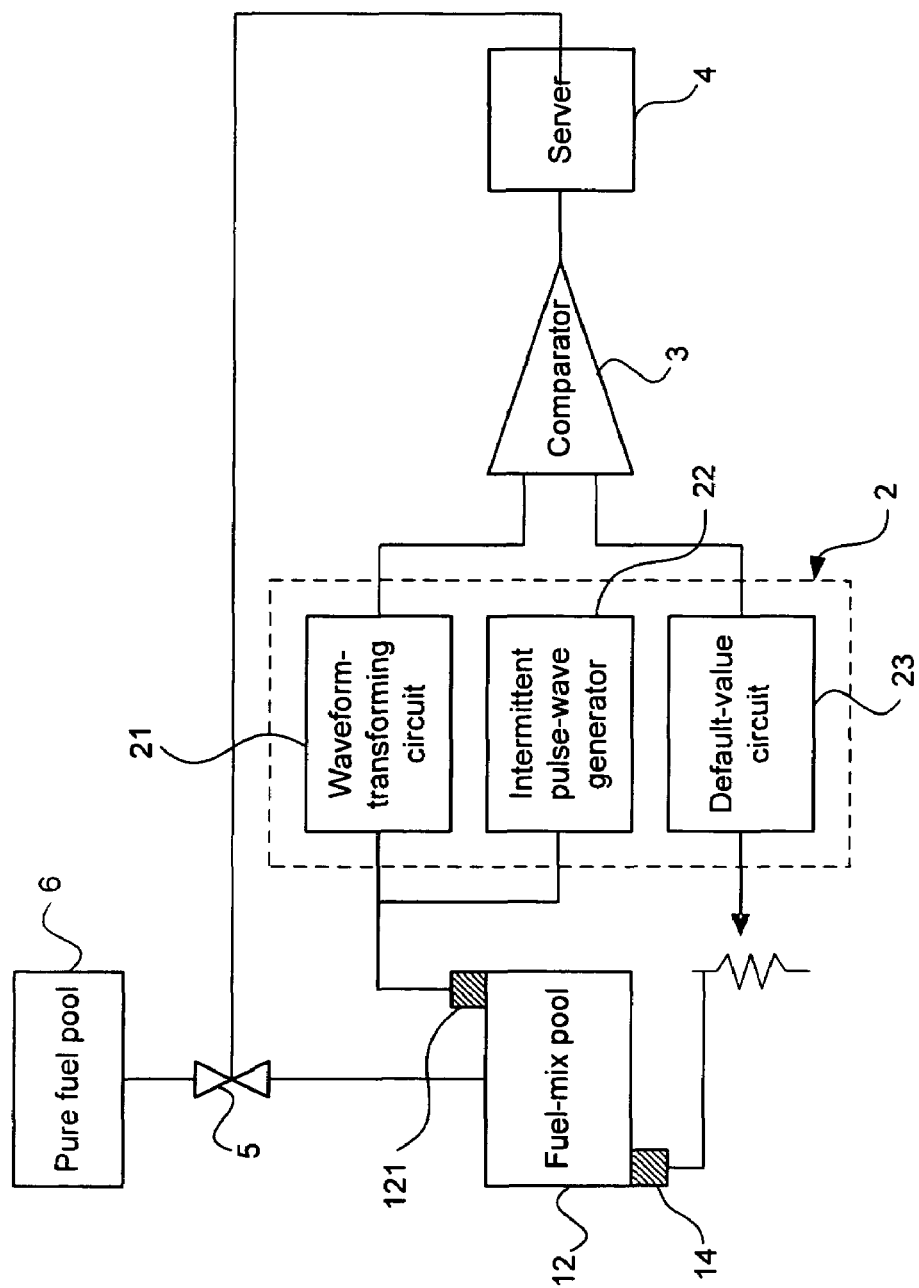

The present invention will be better understood from the following detailed descriptions of the preferred embodiments according to the present invention, taken in conjunction with the accompanying drawings, in which FIG. 1 is a view showing a first preferred embodiment according to the present invention; and FIG. 2 is a view showing a second preferred embodiment according to the present invention.

DESCRIPTION OF THE PREFERRED EMBODIMENTS

The following descriptions of the preferred embodiments are provided to understand the features and the structures of the present invention.

Please refer to FIG. 1, which is a view showing a first preferred embodiment according to the present invention. As shown in the figure, the present invention is a fuel-concentration detecting and controlling device for a fuel cell, comprising a comparative fuel pool 1, an ultrasonic element 2, a comparator 3, a server 4, a controlling device 5 and a pure fuel pool 6. Therein, the comparative fuel pool 1 comprises a standard fuel pool 11 and a fuel-mix pool 12 separated by a barrier 15. The standard fuel pool 11 is filled with a fuel having a standard mixture rate. The barrier 15 is made of a material having high thermal conductivity and no chemical reaction with the fuel for balancing temperatures of the two fuel pools 11, 12. The ultrasonic element 2 comprises a first waveform-transforming circuit 211, a second waveform-transforming circuit 212 and an intermittent-pulse-wave generator 22 generating intermittent ultrasonic waves. The standard fuel pool 11 and the fuel-mix pool 12 are connected with the first waveform-transforming circuit 211 and the second waveform-transforming circuit 212 respectively. A first transducer element 111 is located at a place where the first waveform-transforming circuit 211 is connected with the standard fuel pool 11. A second transducer element 121 is located at a place where the second waveform-transforming circuit 212 is connected with the fuel-mix pool 12. A third transducer element 13 is located between the standard fuel pool 11 and the fuel-mix pool 12 and is connected to the intermittent-pulse-wave generator 22. The first and the second transducer elements 111, 121 have corresponding equidistances to the third transducer element 13. An end of the first transducer element 111 and an end of the second transducer element 121 are connected to an end of the comparator 3. The comparator 3 can be an OP (operational power) amplifier, a transistor or a FLIP-FLOP circuit. Another end of the comparator 3 is connected to an end of the server 4. An amplifier (not shown in the figure) and an A/D (analog/digital) transformer (not shown in the figure) can be further deposed between the comparator 3 and the server 4. Another end of the server 4 is connected to a control part of the controlling device 5. The controlling device 5 can be a uni-directional or bi-directional controlling valve or pump; and the upper and lower ways of the controlling device 5 are connected to the pure fuel pool 6 and the fuel-mix pool 12 respectively. Thus, a novel fuel-concentration detecting and controlling device for a fuel cell is obtained.

In the first embodiment of the present invention, an intermittent-pulse-wave signal is provided by the intermittent-pulse-wave generator 22 to excite the third transducer element 13 by transforming an electrical energy into a mechanical energy to reach the first and the second waveform-transforming circuits 111, 121 through the standard fuel pool 11 and the fuel-mix pool 12 respectively in a form of a longitudinal wave. The longitudinal wave can be an ultrasonic wave. The mechanical energy is then transformed back to the electrical energy to be transmitted to the first and the second waveform-transforming circuits 211, 212 for transforming sine wave into square wave to be transferred to the comparator 5 for a comparison. When the fuel-mix pool 12 comprises the same fuel concentration as the fuel concentration of the standard fuel pool 11, the ultrasonic wave emitted by the third transducer element 13 reach the first and the second transducer elements 111, 121 at the same time without time deviation. When the fuel-mix pool 12 comprises a fuel concentration different from the fuel thickness of the standard fuel pool 11, the ultrasonic wave emitted by the third transducer element 13 reach the first and the second transducer elements 111, 121 at different times with a time deviation. The value of the time deviation is obtained by the comparator 3; and the comparator 3 outputs a control signal to the server 4 accordingly to drive the controlling device 5 for adding fuel from the pure fuel pool 6 to the fuel-mix pool 12 so that the fuel concentration of the standard fuel pool 11 and the fuel concentration of the fuel-mix pool 12 is remain balanced.

Please refer to FIG. 2, which is a view showing a second preferred embodiment according to the present invention. As shown in the figure, the second preferred embodiment replaces the second waveform-transforming circuit 212 of the first preferred embodiment shown in FIG. 1 with a waveform-transforming circuit 21; and replaces the standard fuel pool 11, the first transducer element 111, the third transducer element 13 and the first waveform-transforming circuit 211 of the first preferred embodiment shown in FIG. 1 with an electronic circuit 23 setup with a default value. A thermostat is deposed at the fuel-mix pool 12 for thermo-compensation. So, the second preferred embodiment of the present invention comprises a fuel-mix pool 12, an ultrasonic element 2, a thermostat 14, a comparator 3, a server 4, a controlling device 5 and a pure fuel pool 6. The ultrasonic element 2 comprises the waveform-transforming circuit 21, an intermittent-pulse-wave generator 22, and the electronic circuit 23. The fuel-mix pool 12 is connected to the waveform-transforming circuit 21; and a transducer element 121 is deposed at a place where the waveform-transforming circuit 21 is connected with the fuel-mix pool 12. The transducer element 121 is connected to an end of the intermittent-pulse-wave generator 22; and another end of the waveform-transforming circuit 21 and an end of the electronic circuit 23 are connected to an end of the comparator 3. Another end of the comparator 3 is connected to an end of the server 4; and another end of the server 4 is connected to a control part of the controlling device 5. And, the upper and lower ways of the controlling device 5 are connected with the pure fuel pool 6 and the fuel-mix pool 12 respectively.

In the second embodiment of the present invention, an intermittent-pulse-wave signal is provided by the intermittent-pulse-wave generator 22 to excite the transducer element 121 for transforming electrical energy into mechanical energy to pass the wave signal through the fuel-mix pool 12 in a form of a longitudinal ultrasonic wave. After the ultrasonic wave is reflected back from the wall of the fuel-mix pool 12, the ultrasonic wave is received by the transducer element 121 to be transferred to the waveform-transforming circuit 21 for transforming sine wave into square wave. The wave transformed previously and a time-base signal setup in the electronic circuit 23 for a default fuel concentration are sent together to the comparator 3 for a comparison. When the fuel concentration of the fuel-mix pool 12 is different from the default fuel concentration setup in the electronic circuit 23, the comparator 3 outputs a control signal to the server 4 to drive the controlling device 5 for adding fuel from the pure fuel pool 6 to the fuel-mix pool 12 so that the fuel concentration of the standard fuel pool 11 and the fuel concentration of the fuel-mix pool 12 remains balanced.

The present invention of a fuel-concentration detecting and controlling device for a fuel cell is based on electrochemistry. Please refer to FIG. 1. The fuel concentration of the standard fuel pool 11 is the best fuel concentration for the fuel-mix pool 12. Here a case when the fuel concentration of the fuel-mix pool 12 is lower than of the standard fuel pool 11 is taken. The ultrasonic wave reaches the first and the second transducer elements 111, 121 at different times owing to the different concentration. A comparison between the different times is done by the comparator 3 to obtain a time deviation to drive the controlling device 5 by the server 4 for adding the methanol solution with 100% concentration in the pure fuel pool 6 into the fuel-mix pool to remain the fuel concentration of the fuel-mix pool 12 being between 3.5% and 4%, the same as the fuel concentration of the standard fuel pool 11.

In FIG. 1, the first preferred embodiment of the present invention is able to solve the problem of thermo-variation and electrode contamination by using a barrier 15 between the standard fuel pool 11 and the fuel-mix pool 12 to separate the two pools and to balance the temperatures of the two pools so that the standard fuel pool 11 and the fuel-mix pool 12 are in the same environment. In FIG. 2, the second preferred embodiment of the present invention uses the electronic circuit 23 and the thermostat 14 to solve the same problem. Besides, the first and the second transducer element 111, 121 of the first preferred embodiment are all sensors provided with tiny electricity for reducing cost and minimizing the concentration variation of the fuel-mix pool 12; and the sensor can be an ultrasonic element made through a micro-machine production for a volume minimization.

To sum up, the present invention is a fuel-concentration detecting and controlling device for a fuel cell with reduced cost, minimized volume and increased sensitivity, which controls a concentration of a fuel pool by using a time deviation caused by different concentrations.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A fuel-concentration detecting and controlling device for a fuel cell, comprising:

(a) a comparative fuel pool comprising a standard fuel pool and a fuel-mix pool separated by a barrier balancing temperature between said standard fuel pool and said fuel-mix pool;
(b) an ultrasonic element comprising a first waveform-transforming device, a second waveform-transforming circuit and an intermittent-pulse-wave generator, an end of said first waveform-transforming circuit and an end of said second waveform-transforming circuit connecting respectively with an end of said standard fuel pool and an end of said fuel-mix pool;
(c) a comparator, an end of said comparator connecting with another end of said first waveform-transforming circuit and another end of said second waveform-transforming circuit;
(d) a server, an end of said server connecting with another end of said comparator;
(e) a pure fuel pool; and
(f) a controlling device, a control part of said controlling device connecting with another end of said server, two ways of said controlling device connecting with said pure fuel pool and said comparative fuel pool respectively,
wherein a first transducer element is located at a place said first waveform-transforming circuit is connected with said standard fuel pool; wherein said first transducer element is a piezoelectric element; and wherein said piezoelectric element is a sensor,
wherein a second transducer element is located at a place said second waveform-transforming circuit is connected with said fuel-mix pool; wherein said second transducer element is a piezoelectric element; and wherein said piezoelectric element is a sensor,
wherein a third transducer element is located between said standard fuel pool and said fuel-mix pool and is connected with said intermittent-pulse-wave generator; wherein said third transducer element is a piezoelectric element; and wherein said piezoelectric element is a sensor.

2. The device according to claim 1, wherein said comparator is a device selected from a group consisting of an OP (operational power) amplifier, a transistor and a FLIP-FLOP circuit.

3. The device according to claim 1 wherein said controlling device is a device selected from a group consisting of valve and pump with a direction of ways selected from a group consisting of a uni-direction and a bi-direction.

4. The device according to claim 1 wherein a fuel in said pure fuel pool is a methanol solution.

5. The device according to claim 1, wherein between said comparator and said server is further connected with an amplifier and an A/D (analog/digital) transformer and said A/D transformer is a single chip.

* * * * *